United States Patent
Kimmel et al.

(10) Patent No.: US 12,220,246 B2
(45) Date of Patent: *Feb. 11, 2025

(54) DETECTING SPINAL SHAPE FROM OPTICAL SCAN

(71) Applicants: TECHNION RESEARCH & DEVELOPMENT FOUNDATION LIMITED, Haifa (IL); NEW YORK SOCIETY FOR THE RELIEF OF THE RUPTURED AND CRIPPLED, MAINTAINING THE HOSPITAL FOR SPECIAL SURGERY, New York, NY (US)

(72) Inventors: Ron Kimmel, Haifa (IL); Benjamin Groisser, Haifa (IL); Alon Wolf, Haifa (IL); Roger F. Widmann, New York, NY (US); Howard J. Hillstrom, New York, NY (US)

(73) Assignees: TECHNION RESEARCH & DEVELOPMENT FOUNDATION LIMITED, Haifa (IL); NEW YORK SOCIETY FOR THE RELIEF OF THE RUPTURED AND CRIPPLED, MAINTAINING THE HOSPITAL FOR SPECIAL SURGERY, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/652,432

(22) Filed: May 1, 2024

(65) Prior Publication Data
US 2024/0277283 A1    Aug. 22, 2024

Related U.S. Application Data

(63) Continuation of application No. 17/271,687, filed as application No. PCT/IL2019/050969 on Aug. 28, 2019, now Pat. No. 12,016,697.

(Continued)

(51) Int. Cl.
A61B 5/00    (2006.01)
G06T 7/00    (2017.01)
G06T 17/20   (2006.01)

(52) U.S. Cl.
CPC .......... *A61B 5/4566* (2013.01); *G06T 7/0012* (2013.01); *G06T 17/20* (2013.01);
(Continued)

(58) Field of Classification Search
CPC ..... A61B 5/4566; G06T 7/0012; G06T 17/20; G06T 2200/08; G06T 2207/10028;
(Continued)

(56) References Cited

U.S. PATENT DOCUMENTS

2014/0303522 A1   10/2014   Akimoto et al.
2016/0203361 A1   7/2016    Black et al.

FOREIGN PATENT DOCUMENTS

WO    2017141958 A1    8/2017

OTHER PUBLICATIONS

Bendels, G. H., Klein, R., Samimi, M., & Schmitz, A. (2005). Statistical shape analysis for computer aided spine deformity detection. Journal of WSCG. 2005, vol. 13, No. 2, p. 57-64. Available online: [http://hdl.handle.net/11025/1442].

(Continued)

*Primary Examiner* — Casey L Kretzer
(74) *Attorney, Agent, or Firm* — The Roy Gross Law Firm, LLC; Roy Gross

(57) ABSTRACT

A method comprising: generating a parametrized three-dimensional (3D) body surface model on a training set comprising a plurality of 3D scans of subjects, wherein at least some of said 3D scans are of subjects having a skeletal deformity; receiving one or more target 3D scans of a target subject; optimizing said body surface model with respect to said one or more target 3D scans to calculate a target body (Continued)

surface model of said target subject; training a skeletal estimation model on a training set comprising: (i) body surface models of a plurality of subjects, and (ii) skeletal landmarks sets of said plurality of subjects; and applying said trained skeletal estimation model to said calculated target body surface model of said target subject, to estimate a skeletal shape of said target subject.

18 Claims, 7 Drawing Sheets

Related U.S. Application Data

(60) Provisional application No. 62/723,598, filed on Aug. 28, 2018.

(52) U.S. Cl.
CPC ...... *G06T 2200/08* (2013.01); *G06T 2207/10028* (2013.01); *G06T 2207/20081* (2013.01); *G06T 2207/20084* (2013.01); *G06T 2207/20101* (2013.01); *G06T 2207/30012* (2013.01); *G06T 2210/41* (2013.01)

(58) Field of Classification Search
CPC . G06T 2207/20081; G06T 2207/20084; G06T 2207/20101; G06T 2207/30012; G06T 2210/41
See application file for complete search history.

(56) References Cited

OTHER PUBLICATIONS

Groisser B, Kimmel R, Feldman G, Rozen N, Wolf A. 3D Reconstruction of Scoliotic Spines from Stereoradiography and Depth Imaging. Ann Biomed Eng. Aug. 2018;46(8):1206-1215. doi: 10.1007/s10439-018-2033-7. Epub Apr. 23, 2018. PMID: 29687237.
Pazos V, Cheriet F, Song L, Labelle H, Dansereau J. Accuracy assessment of human trunk surface 3D reconstructions from an optical digitising system. Med Biol Eng Comput. Jan. 2005;43(1):11-5. doi: 10.1007/BF02345117. PMID: 15742714.
Roy S, Grunwald ATD, Alves-Pinto A, Maier R, Cremers D, Pfeiffer D, Lampe R. A Noninvasive 3D Body Scanner and Software Tool towards Analysis of Scoliosis. Biomed Res Int. May 9, 2019;2019:4715720. doi: 10.1155/2019/4715720. PMID: 31211138; PMCID: PMC6532313.
Matthew Loper, Naureen Mahmood, Javier Romero, Gerard Pons-Moll, and Michael J. Black. 2015. SMPL: a skinned multi-person linear model. ACM Trans. Graph. 34, 6, Article 248 (Nov. 2015), 16 pages. https://doi.org/10.1145/2816795.2818013.
F. Bogo, J. Romero, M. Loper and M. J. Black, "FAUST: Dataset and Evaluation for 3D Mesh Registration," 2014 IEEE Conference on Computer Vision and Pattern Recognition, 2014, pp. 3794-3801, doi: 10.1109/CVPR.2014.491.
Brett Allen, Brian Curless, and Zoran Popović. 2003. The space of human body shapes: reconstruction and parameterization from range scans. ACM Trans. Graph. 22, 3 (Jul. 2003), 587-594. https://doi.org/10.1145/882262.882311.
Suzuki, N, Ono T, Tezuka, M, Kamiishi, S: Moire Topography and Back shape Analysis Clinical Application: International Symposium on 3-D Scoliotic Deformity. ed. by J. Dansereau, Gustav Fischer Verlag, Montreal, 124-130, 1992.
Betsch M, Schneppendahl J, Dor L, Jungbluth P, Grassmann JP, Windolf J, Thelen S, Hakimi M, Rapp W, Wild M. Influence of foot positions on the spine and pelvis. Arthritis Care Res (Hoboken). Dec. 2011;63(12):1758-65. doi: 10.1002/acr.20601. PMID: 22127967.
Amendt LE, Ause-Ellias KL, Eybers JL, Wadsworth CT, Nielsen DH, Weinstein SL. Validity and reliability testing of the Scoliometer. Phys Ther. Feb. 1990;70(2):108-17. doi: 10.1093/ptj/70.2.108. PMID: 2296610.
K. Reinhardt, Über die Zerlegung der Ebene in Polygone. Dissertation, Univ. Frankfurt a. M. Noske, Borna-Leipzig 1918. Available online: [http://resolver.sub.uni-goettingen.de/purl?PPN316479497].
Panjabi MM, Brand RA Jr, White AA 3rd. Three-dimensional flexibility and stiffness properties of the human thoracic spine. J Biomech. 1976;9(4):185-92. doi: 10.1016/0021-9290(76)90003-8. PMID: 1262353.
Gerchberg, R.W. (1972). A practical algorithm for the determination of phase from image and diffraction plane pictures. Optik, 35, 237-246.
Kane WJ. Scoliosis prevalence: a call for a statement of terms. Clin Orthop Relat Res. Jul.-Aug. 1977;(126):43-6. PMID: 598138.
Grünbaum, Branko; Shephard, G. C. (1980). Tilings with congruent tiles. Bulletin of the American Mathematical Society, 3(3), 951-974. doi: 10.1090/S0273-0979-1980-14827-2.
E. Hierholzer; G. Lüxmann (1982). Three-dimensional shape analysis of the scoliotic spine using invariant shape parameters. , 15(8), 583-598. doi:10.1016/0021-9290(82)90070-7.
Robin GC, Span Y, Steinberg R, Makin M, Menczel J. Scoliosis in the elderly: a follow-up study. Spine (Philadelphia, PA, 1976). Jul.-Aug. 1982;7(4):355-9. doi: 10.1097/00007632-198207000-00005. PMID: 6215719.
W. Frobin; E. Hierholzer (1982). Analysis of human back shape using surface curvatures. , 15(5), 379-390. doi: 10.1016/0021-9290(82)90059-8.
B. Drerup (1984). Principles of measurement of vertebral rotation from frontal projections of the pedicles. , 17(12), 923-935. doi:10.1016/0021-9290(84)90005-8.
Pearcy, M. J. (1985). Stereo radiography of lumbar spine motion. Acta Orthopaedica, 56(s212), 1-45. doi:10.3109/17453678509154154.
Drerup B, Hierholzer E. Objective determination of anatomical landmarks on the body surface: measurement of the vertebra prominens from surface curvature. J Biomech. 1985;18(6):467-74. doi: 10.1016/0021-9290(85)90282-9. PMID: 4030803.
E. Hierholzer "Analysis Of Left-Right Asymmetry Of The Back Shape Of Scoliotic Patients", Proc. SPIE 0602, Biostereometrics '85, (Jul. 7, 1986); https://doi.org/10.1117/12.956324.
Drerup B. Improvements in measuring vertebral rotation from the projections of the pedicles. J Biomech. 1985;18 (5):369-78. doi: 10.1016/0021-9290(85)90292-1. PMID: 4008507.
Wood GA, Marshall RN. The accuracy of DLT extrapolation in three-dimensional film analysis. J Biomech. 1986;19 (9):781-5. doi: 10.1016/0021-9290(86)90201-0. PMID: 3793752.
Rumelhart, David E.; Hinton, Geoffrey E.; Williams, Ronald J. (1986). Learning representations by back-propagating errors. , 323(6088), 533-536. doi:10.1038/323533a0.
Drerup B, Hierholzer E. Automatic localization of anatomical landmarks on the back surface and construction of a body-fixed coordinate system. J Biomech. 1987;20(10):961-70. doi: 10.1016/0021-9290(87)90325-3. PMID: 3693377.
Carter OD, Haynes SG. Prevalence rates for scoliosis in US adults: results from the first National Health and Nutrition Examination Survey. Int J Epidemiol. Dec. 1987;16(4):537-44. doi: 10.1093/ije/16.4.537. PMID: 3501989.
Drerup B, Hierholzer E. Movement of the human pelvis and displacement of related anatomical landmarks on the body surface. J Biomech. 1987;20(10):971-7. doi: 10.1016/0021-9290(87)90326-5. PMID: 3693378.
Dansereau J, Stokes IA. Measurements of the three-dimensional shape of the rib cage. J Biomech. 1988;21 (11):893-901. doi: 10.1016/0021-9290(88)90127-3. PMID: 3075610.
E. Hierholzer, B. Drerup, "Assessment Of Three-Dimensional Scoliotic Deformity By Rasterstereography," Proc. SPIE 1030, Biostereometrics '88, (Apr. 14, 1989); https://doi.org/10.1117/12.950448.
Gardner Martin. 1988. Time Travel and Other Mathematical Bewilderments. New York: W.H. Freeman.
Stokes IA, Shuma-Hartswick D, Moreland MS. Spine and back-shape changes in scoliosis. Acta Orthop Scand. Apr. 1988;59(2):128-33. PMID: 3364179.

(56) References Cited

OTHER PUBLICATIONS

Adams LP, Constant DA. Biostereometrics in the study of the morphology of the lumbar sacral spine. Med Biol Eng Comput. Jul. 1988;26(4):383-8. doi: 10.1007/BF02442296. PMID: 3255846.

Turner-Smith AR, Harris JD, Houghton GR, Jefferson RJ. A method for analysis of back shape in scoliosis. J Biomech. 1988;21(6):497-509. doi: 10.1016/0021-9290(88)90242-4. PMID: 3209594.

B. Drerup and E. Hierholzer "Description Of Scoliotic Deformity Pattern By Harmonic Functions", Proc. SPIE 1030, Biostereometrics '88, (Apr. 14, 1989); https://doi.org/10.1117/12.950447.

Choi, R., Watanabe, K., Jinguji, H., Fujita, N., Ogura, Y., Demura, S., Kotani, T., Wada, K., Miyazaki, M., Shigematsu, H., & Aoki, Y. (2017). CNN-based Spine and Cobb Angle Estimator Using Moire Images.

Choi, R., Watanabe, K., Fujita, N., Ogura, Y., Matsumoto, M., Demura, S., Kotani, T., Wada, K., Miyazaki, M., Shigematsu, H., & Aoki, Y. (2018). Measurement of Vertebral Rotation from Moire Image for Screening of Adolescent Idiopathic Scoliosis.

PCT International Search Report for International Application No. PCT/IL2019/050969, mailed Dec. 24, 2019, 4pp.

PCT Written Opinion for International Application No. PCT/IL2019/050969, mailed Dec. 24, 2019, 5pp.

PCT International Preliminary Report on Patentability for International Application No. PCT/IL2019/050969, issued Mar. 2, 2021, 6pp.

DETECTING SPINAL SHAPE FROM OPTICAL SCAN

CROSS REFERENCE TO RELATED APPLICATIONS

This application is a Continuation of U.S. patent application Ser. No. 17/271,687, filed Feb. 26, 2021, which is a National Phase of PCT Patent Application No. PCT/IL2019/050969 having International filing date of Aug. 28, 2019, which claims the benefit of priority from U.S. Provisional Patent Application No. 62/723,598, filed on Aug. 28, 2018, entitled "MOTION CORRECTION FOR SLOT SCANNERS USING SURFACE MEASUREMENTS", the contents of which are all incorporated by reference herein in their entirety.

FIELD OF INVENTION

The invention relates to the field of image processing and deep learning.

BACKGROUND OF THE INVENTION

Adolescent Idiopathic Scoliosis (AIS) is a prevalent disease that currently requires radiographic imaging for accurate diagnosis and treatment planning.

For diagnosis, monitoring, therapeutic planning, and epidemiologic analysis of scoliosis, images of the spine are required. Imaging modalities such as radiography, computed tomography (CT) and magnetic resonance (MR) imaging are commonly used, where radiography plays the primary role.

Beyond the health risks associated with repeated radiography, standard x-rays suffer from the inherent limitation of providing a two-dimensional projection of a three-dimensional structure, and a variety of trunk surface metrics have been devised to complement the Cobb angle in characterizing thoracic deformity.

Despite the prevalence of the disease, and the carcinogenic effect of repeated exposure to ionizing radiation, there is currently no accurate test for scoliosis outside of radiography. Accordingly, accurate non-invasive diagnostic technique would enable screening for scoliosis with less exposure to radiation.

The foregoing examples of the related art and limitations related therewith are intended to be illustrative and not exclusive. Other limitations of the related art will become apparent to those of skill in the art upon a reading of the specification and a study of the figures.

SUMMARY OF THE INVENTION

The following embodiments and aspects thereof are described and illustrated in conjunction with systems, tools and methods which are meant to be exemplary and illustrative, not limiting in scope.

There is provided, in an embodiment, a method comprising: generating a parametrized three-dimensional (3D) body surface model, based, at least in part, on a training set comprising a plurality of 3D scans of subjects, wherein at least some of said 3D scans are of subjects having a skeletal deformity; receiving one or more target 3D scans of a target subject; optimizing said body surface model with respect to said one or more target 3D scans, based, at least in part, on minimizing a loss function which registers said body surface model to said target 3D scans, to calculate a target body surface model of said target subject; training a skeletal estimation model, based, at least in part, on a training set comprising: (i) body surface models of a plurality of subjects, and (ii) skeletal landmarks sets of said plurality of subjects; and applying said trained skeletal estimation model to said calculated target body surface model of said target subject, to estimate a skeletal shape of said target subject.

There is also provided, in an embodiment, a system comprising: at least one hardware processor; and a non-transitory computer-readable storage medium having stored thereon program code, the program code executable by the at least one hardware processor to: generate a parametrized three-dimensional (3D) body surface model, based, at least in part, on a training set comprising a plurality of 3D scans of subjects, wherein at least some of said 3D scans are of subjects having a skeletal deformity, receive one or more target 3D scans of a target subject, optimize said body surface model with respect to said one or more target 3D scans, based, at least in part, on minimizing a loss function which registers said body surface model to said target 3D scans, to calculate a target body surface model of said target subject, train a skeletal estimation model, based, at least in part, on a training set comprising: (i) body surface models of a plurality of subjects, and (ii) skeletal landmarks sets of said plurality of subjects, and apply said trained skeletal estimation model to said calculated target body surface model of said target subject, to estimate a skeletal shape of said target subject.

There is further provided, in an embodiment, a computer program product comprising a non-transitory computer-readable storage medium having program code embodied therewith, the program code executable by at least one hardware processor to: generate a parametrized three-dimensional (3D) body surface model, based, at least in part, on a training set comprising a plurality of 3D scans of subjects, wherein at least some of said 3D scans are of subjects having a skeletal deformity; receive one or more target 3D scans of a target subject; optimize said body surface model with respect to said one or more target 3D scans, based, at least in part, on minimizing a loss function which registers said body surface model to said target 3D scans, to calculate a target body surface model of said target subject; train a skeletal estimation model, based, at least in part, on a training set comprising: (i) body surface models of a plurality of subjects, and (ii) skeletal landmarks sets of said plurality of subjects; and apply said trained skeletal estimation model to said calculated target body surface model of said target subject, to estimate a skeletal shape of said target subject.

In some embodiments, at least some of said target 3D scans are labelled with a pose of said subject associated with a respective target 3D scan.

In some embodiments, said training of said 3D body surface model is configured to encode a body type parameter, based, at least in part, on a labeling of said training set with said skeletal deformity.

In some embodiments, said labelling is a scoliosis classification category selected from the group consisting of: main thoracic, double thoracic, double/triple major, and thoracolumbar/lumbar.

In some embodiments, said encoding is a low-dimensional encoding.

In some embodiments, said 3D body scan comprises at least one of: a point cloud, triangulated meshes, and splined surfaces.

In addition to the exemplary aspects and embodiments described above, further aspects and embodiments will become apparent by reference to the figures and by study of the following detailed description.

BRIEF DESCRIPTION OF THE DRAWINGS

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Figure 1:
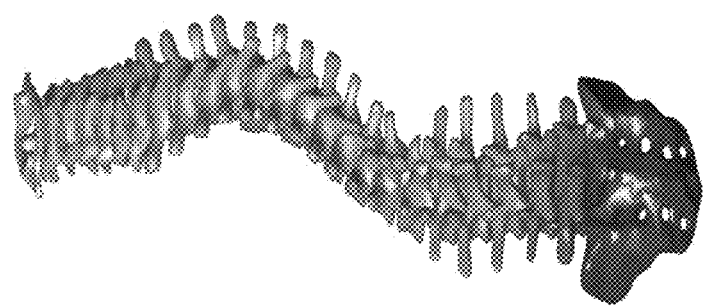
FIG. 1 shows an image of parametric spine model, according to exemplary embodiments of the present invention.

Described herein are a system, method, and computer program product for predicting spinal shape of a human subject from a three-dimensional (3D) surface scan of the subject. In some embodiments, the prediction of the spine shape can involve applying one or more trained neural network algorithms.

In some embodiments, the present disclosure provides for detecting a spine shape of a human subject, based on a 3D surface scan of said subject (e.g., a depth map of the subject). In some embodiments, diverse technologies and technique from the field of three-dimensional (3D) graphics may be utilized to depict the human subjects. In some embodiments, these models can be represented in 3D coordinates that define the positions of surface elements representing the surface of an object in a 3D space, as elaborated further below.

In some embodiments, the present disclosure provides for analyzing the three-dimensional image to predict the spine shape of a human subject in a multi-step process which may involve diverse training methods of neural network algorithms.

In some embodiments, the present disclosure provides for generating a computerized parametrized three-dimensional (3D) body surface model which encodes various body type parameters, such as, e.g., those reflecting various skeletal and/or spinal deformities, such as scoliosis. In some embodiments, the 3D model may be trained, based, at least in part, on a training set comprising a plurality of 3D scans of subjects, wherein at least some of the 3D scans are of subjects having a skeletal deformity.

In some embodiments, the 3D model may be personalized for a specified target subject, by a process of optimization based on one or more 3D scans of the target subject. In some embodiments, at least some of the 3D scans are associated with various poses of the subject during the scan. In some embodiments, the optimization is performed by minimizing a loss function which registers the 3D model to the target 3D scans.

In some embodiments, the present disclosure may further provide for training a computerized skeletal estimation model to accurately estimate a skeletal shape of a subject from a 3D surface scan. In some embodiments, the computerized skeletal estimation model may be trained on a training set comprising body surface models of a plurality of subjects, and skeletal landmarks sets of the same subjects. In some embodiments, the training process of the skeletal estimation model may comprise a usage of a spine models defining the shape of the spinal cords of a human body. Thus, the training sets for the training stage of the skeletal estimation model may comprise a plurality of body surface models of human subjects, and spine models defining shapes of spinal cords. In some embodiments, the spine models may be utilized to train the skeletal estimation model to predict the spine shape in a given surface model of a human subject. In some embodiments, the training process to predict the spine shapes in a subject surface may involve optimization process utilized to identify the geometric relationship between at least one spine model and each body surface model in a given training set. In some embodiments, such a training process can train the skeletal estimation model to predict the spine shape in a body surface model given as an input at the inference stage.

In some embodiments, the trained computerized skeletal estimation model may be then applied to the personalized body model of the target subject, to estimate a skeletal shape of the target subject.

In some embodiments, the results may be used by clinicians to visualize skeletal body shape in 3D, for a fast, accurate, and safe diagnosis and treatment planning.

In some embodiments, the full analysis process for predicting the spine shape of a human subject may require a two-step process which involves, first, calculating a model of a parametrized three-dimensional body surface by applying the optimized and personalized neural network algorithm to a three-dimensional scan of a human subject. Then, applying the skeletal estimation model to the calculated three-dimensional body surface model, to predict the spine shape of that subject.

In some embodiments, the three-dimensional scan of a human subject utilized in the two-step process mentioned above, can be produced by an optical scanning system which requires no ionizing radiation, e.g., by depth cameras.

Radiographic Assessment of Scoliosis

Scoliosis is the most common spinal deformity in adolescents, and in the United States affects up to 5% of adolescents (about two million), 8% adults (16 million), and 70% of the elderly.

The clinical definition of scoliosis is Cobb angle of above 10 in the coronal plane. A more expressive classification system for describing scoliosis is the Lenke scale. In the simplest use case, Lenke classification divides scoliosis patients into six categories based on spine structure and function e.g. "Main Thoracic", "Double Major", "Triple Major", etc.

Parametrized Skeletal Models

A parameterized model describes different members of a class (e.g. spine shapes) using a shared framework. A simple model of the human spine ignores morphology of individual vertebrae and instead merely describes the rigid body rotations between bones. By collecting a large representative training set and using dimensionality reduction, this method has been used to develop robust statistical models of scoliotic deformity with only five or ten parameters. An even simpler (and less descriptive) parameterization of the spine would be a one-dimensional curve that passes through the center of the vertebral bodies, though this would not even capture axial rotation.

Description of Proposed Methods

In some embodiments, the present disclosure is based on the notion that surface body topography carries sufficient information to accurately estimate skeletal shape. A critical distinction is that the proposed methods seek to extract as much information as possible from surface scans by employing full-body modeling that accounts for and encodes pathological body types and variable postures.

Specifically, the methods proposed herein can provide an accurate estimate of an individual subject's spine pose, using shape parameters from a personalized body model. Furthermore, the present disclosure proposes a hypothesis that these parameters can be fitted to optical scans (e.g., depth clouds).

This proposal is divided into four sections:
(i) General Surface Model Encoding Poses and Pathologies: This is a statistical model of human body shapes that can describe people in arbitrary poses and accounts for pathological body types (e.g., scoliotic body types). This model can be trained from a training set of optical scans of normal and pathological subjects.
(ii) Model Personalization: Optimizing the general model to calculate a target body surface model of said target subject;
(iii) Skeletal Estimation from Surface: This is a statistical model that provides an estimate of bone positions from a known 3D surface shape. This model can be trained with a training set of corresponding optical and radiographic scans.
(iv) Assessment and Visualization: Applying the trained skeletal estimation model to estimate a skeletal shape of the target subject.

Figure 2:
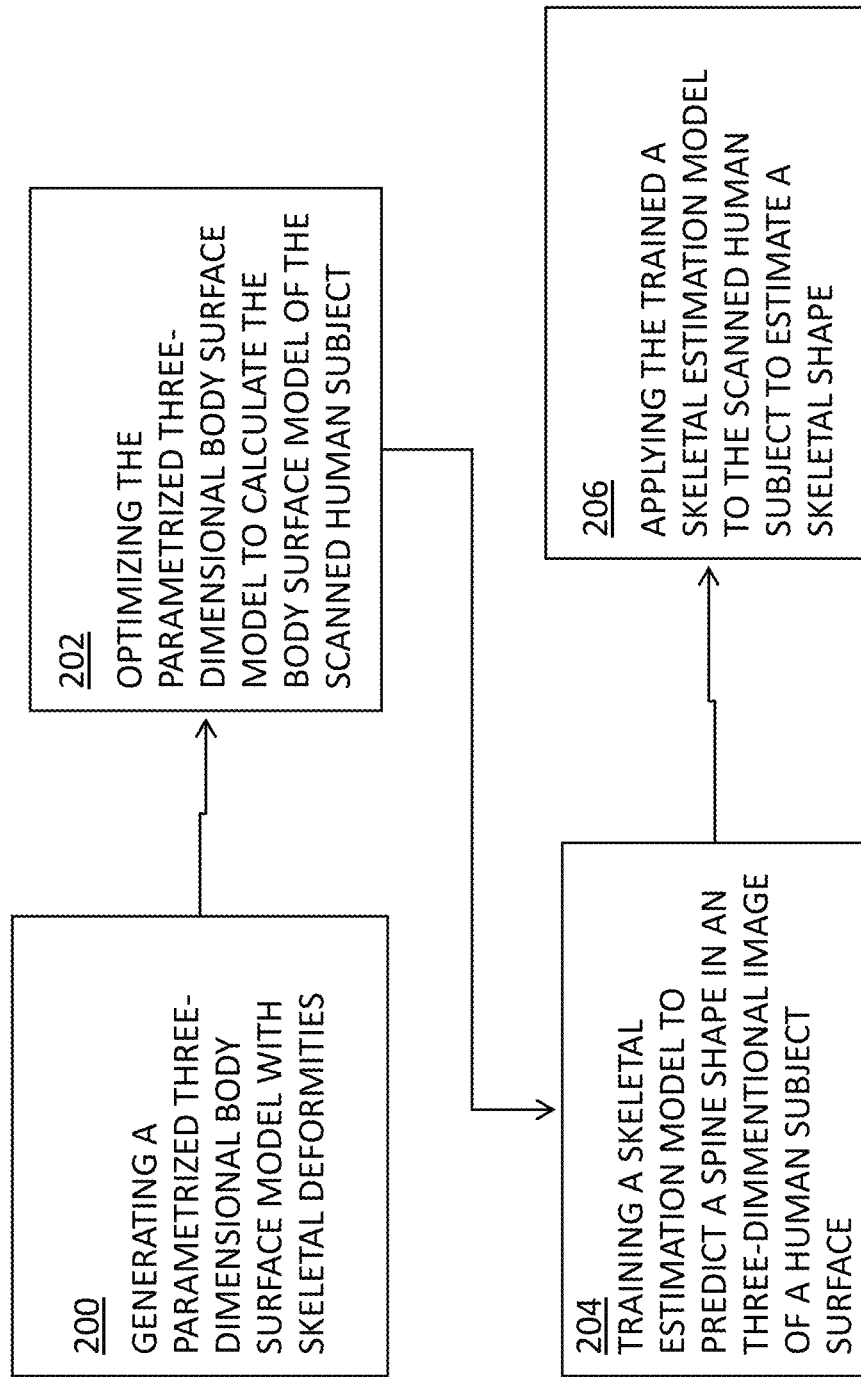
FIG. 2 is a flowchart of the functional steps in a method for estimating spinal shape of a subject from an optical scan, according to exemplary embodiments of the present invention.

FIG. 2 is a flowchart of the functional steps in a method for estimating spinal shape of a subject from an optical scan, according to exemplary embodiments of the present invention.

Parametrized Body Shape Model

At step 200, a computerized parametrized three-dimensional (3D) body surface model is trained, based, at least in part, on a training set comprising a plurality of 3D scans of subjects. In some embodiments, at least some of the 3D scans are of subjects having a skeletal deformity.

In some embodiments, generating such a training set can be based on a computer animation-based model utilized to generate sets of three-dimensional images depicting human subjects in arbitrary poses. In some embodiments, graphics applications can utilize publicly available databases of three-dimensional human shapes for generating such a wide variety of human bodies in a variety of shapes at arbitrary poses.

In some embodiments, the representation of human subjects can be using skinned vertex-based models which accurately represent a wide variety of body shapes in natural human poses, e.g., Skinned Multi-Person Linear model (SMPL).

In some embodiments, other models which span variations in both body shapes and poses such as Shape Completion and Animation of People (SCAPE) can be used.

In some embodiments, the models utilized to define the training set, and or training sets, may be based on normal (e.g., bodies which don't manifest any pathologies) and bodies manifesting spine deformations and/or pathologies.

In some embodiments, other technologies and models that accurately represent a wide variety of body shapes in natural human poses can be used. E.g., in some embodiments, a technology based on surface mesh may be used for that purpose. For example, the surface shape may be provided by collections of vertices, edges and faces which define the shape of a surface. In some embodiments, each surface element may be represented a three-dimensional coordinate system.

In some embodiments, diverse models may utilize different methods and technologies to express surface shapes and surface deformations. In some embodiments, these models may be based on a mesh of surface elements to represent the surface shape of a human subject. In some embodiments, such surface elements can be based on triangle deformations, wherein the surface is represented in diverse techniques such as, triangle mesh, vertex-based model, and the like.

In some embodiments, generating the training sets may also comprise using models of human subjects resulting from optical scans of both, bodies with no pathologies and bodies with pathologies.

In some embodiments, the training set and/or training sets with the images can be used to build input data comprising body type parameters for artificial neural network algorithm. In some embodiments, diverse techniques and neural network algorithms can be utilized as elaborated here below.

In M. Loper, N Mahmood, and J Romero. SMPL: a skinned multi-person linear model. ACM Transactions, on Graphics, 34(6), 2015, it was shown the Standard Blend Skinning models from computer animation can be "corrected" with linear models learned from body scan data. The result is a state-of-the-art model that shows comparable or superior generalizability to previously published work and is significantly faster to render. The general expression for linear blend skinning is given by the following equations $$T_v = \sum_{k=1}^{k} \omega_{k,v} G'(\theta, J) T_v^* \quad (1)$$

$$G'_k(\theta, J) = G_k(\theta, J) G_k(\theta^*, J) \quad (2)$$

$$G_k(\theta, J) = \prod_{j \in A(k)} \begin{bmatrix} R(\omega j) & J_j \\ 0 & 1 \end{bmatrix} \quad (3)$$

where w is a blend weight for each vertex v over all K joints, and θ is the pose as in SCAPE. $G_0$ is the homogeneous transformation matrix that moves template vertex $T_v^*$ to posed position $T_v$, and is formed by a series of local transformations around sequential joints with global coordinates J. R(ω) is the rotation matrix for angle-axis ω.

The innovation that Loper et al. introduce is to learn a set of body type parameters D and pose parameters Q to modify the template Tv before applying the blended pose transformation.

$$T_v^* = \bar{T}_v + D(\beta) + Q(\theta) \quad (4)$$

Here β is a low dimensional encoding of subject shape. The specific representation D is flexible. For example, a PCA, as elaborated further below, but this can be adapted to better suit the needs of a training set including deformity. In some embodiments, Q(θ) also has room for modification. In some embodiments, a linear combination of elements of the elements of $R(\theta)$ can be used but as noted in the literature, this too is open to experimentation.

Deformity Parameterized Body Model

SCAPE and SMPL are sophisticated models, but they both make an approximation that all humans deform analogously due to pose. This assumption is decidedly not true for scoliotic subjects. Indeed, measurements of trunk angle by scoliometer and the Adams bending test are predicated on research showing that scoliotic subjects do not deform like healthy subjects in a forward bending pose.

In some embodiments, to encode this relation, it may be necessary to update these deformation models to include a dependence on body type, such that pose deformations depend both on pose angles $\theta$ and body type $\beta$. For example, a linear blend of models weighted by body type parameters $\beta$:

$$Q_v = \sum_{i=1}^{|\beta|} \beta_i \cdot P_i vec(R(\theta)) \qquad (5)$$

where $P_i$ is a matrix of learned parameters, and $vec(R(\theta))$ is the column-stacked elements of all rotation's matrices in the model.

Given a training set of surface scans, model parameters P, w, T, and J can be learned by iteratively finding registrations that best match scans as well as model parameters. In some embodiments, this can be formulated as a minimization of an objective function across all subjects and all scans.

In some embodiments, other potentially nonlinear formulations for Q may be utilized. For each vertex, $Q_v(\beta,\theta)$ is a 3×1 displacement vector. This function could for example be modeled with a simple feed-forward network.

$$Q_v = U_v \phi(W_v vec(\beta, \theta) + a_v) + b_v \qquad (6)$$

wherein $W_v$, $U_v$ are weight matrices, $a_v$, $b_v$ are bias vectors, and $\varphi$ is a nonlinear function such as tanh. The specific architecture of the network may not be important.

In some embodiments, regardless of the specific formulation, this body model presents a significant innovation: Using body type parameters $\beta$ that are specifically learned from pathologic subjects. The promise of this method is that, given a set of examples for training, it will be possible to model the expected deformations based on individual body type as characterized by $\beta$.

This, in turn, should also enable more accurate assessments of novel subjects: When performing nonrigid mesh registrations to fit optical scans of a novel subject, the registration will be guided by the deformations expected by the model. In this way, the registration process itself will perform the first step in characterizing scoliotic deformity.

Low Dimensional Body Parameters

As previously mentioned, part of a successful model can be properly defining $\beta$, individual subject shape in low dimensional space. In some embodiments, the simplest approach can be to project D into PCA space (principal component analysis) using all scoliotic and non-scoliotic subjects as the basis. This approach may probably work reasonably well but note that PCA is optimal for Gaussian variance while a training set of normal and scoliotic subjects is not expected to follow this distribution.

In some embodiments, a combination of PCA and Linear Discriminant Analysis (LDA) is proposed. In some embodiments, the idea is to concentrate deformity into a few parameters, while still allowing the model to generalize well across populations. To apply this technique to scoliotic body modeling, PCA will first be performed on subjects with less than 10 spine curves, potentially including public training sets. The scoliotic population will then be projected onto the first few Principle Shape Components (PSC), corresponding to the axes of greatest variance in the normal population. These projections will be subtracted from the scoliotic population according to the Gram-Schmidt algorithm, leaving a residual characterized largely by scoliotic deformity.

In some embodiments, the scoliotic training set can then be labeled, for example into four simplified Lenke categories:

Main thoracic
Double thoracic
Double/Triple Major
Thoracolumbar/Lumbar.

In some embodiments, using the full Lenke classification would require bending radiographs, but the merged categories only account for 6% of AIS patients. With these labels, the entire cohort can be processed with LDA to generate a set of coefficients representing scoliotic deformity. In this paradigm we anticipate defining $\beta$ as perhaps the first four PCA PSCs as well as four classes for LDA.

High-Resolution Optical Scans

Figure 3:
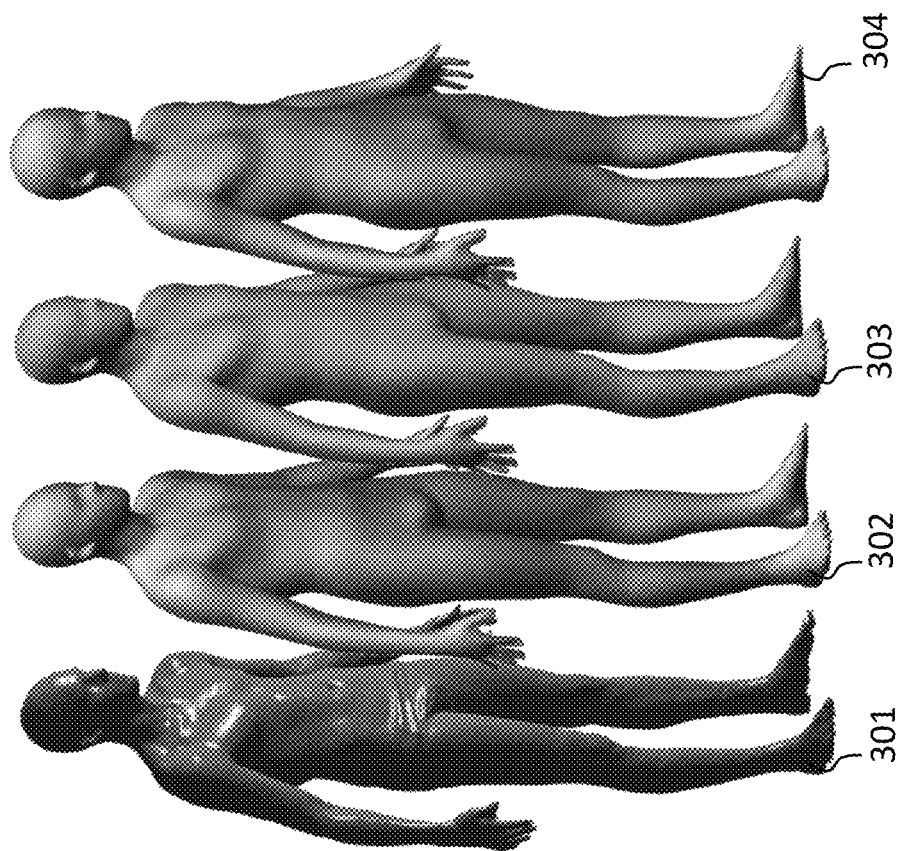
FIG. 3 is an illustration of low-dimensional surface parameterizations, according to exemplary embodiments of the present invention.

FIG. 3 is an illustration of low-dimensional surface parameterizations. Surface scan 301 is received from an existing dataset (e.g., Federica Bogo, Javier Romero, Matthew Loper, and Michael J. Black. FAUST: Dataset and evaluation for 3D mesh registration. Proceedings of the IEEE Computer Society Conference on Computer Vision and Pattern Recognition, pages 3794-3801, 2014). A nonrigid mesh registration to surface scan 302 may then be generated, followed by a low-dimensional PCA representation 303 using 4 PSCs. Finally, s semantic encoding 304 is created, similar to, e.g., Brett Allen, Brian Curless, and Z Popovic. The space of human body shapes: reconstruction and parameterization from range scans. ACM Transactions on Graphics, 22(3):587-594, 2003).

Figure 4:
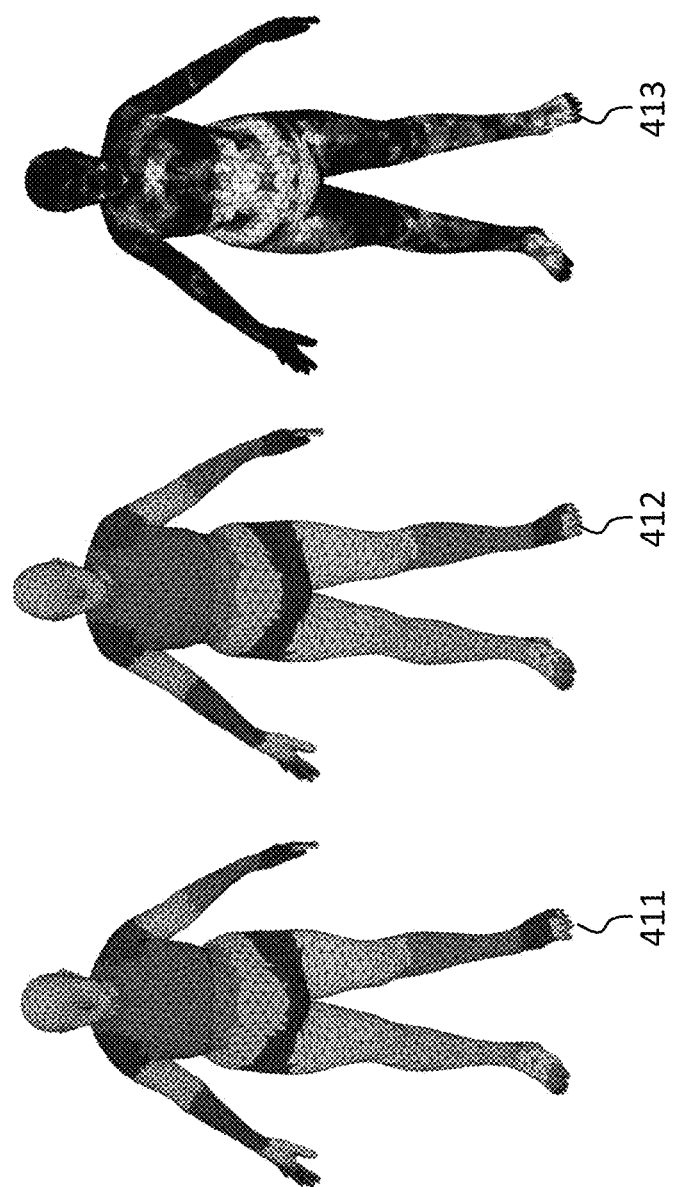
FIG. 4 shows residual of PCA representation of subject from FAUST, according to exemplary embodiments of the present invention.

FIG. 4 shows a registered surface mesh 411, a PCA representation 412, and a PCA residual 413. In some embodiments, the PCA residual 413 can be utilized as inputs to LDA decomposition. In some cases, for this non-pathologic subject, the residuals are largely symmetric.

In some embodiments, full-body surface representation can be provided by a system employing an array of depth cameras. In some embodiments, such a system can utilize the images captured by the depth camera to produce a multi-dimensional surface representation of the optically scanned body. In some embodiments, such can be based on surface mesh which represent the body in vertices, edges and faces which define the shape of the body surface.

In some embodiments, the vertices of the surface representation are defined in a unified coordinate system. In some embodiments, the unified coordinate system can provide the positions of the vertices for generating a vector representation of the human subjects.

In some embodiments, the specific technology used to collect surface scans is not important, and several viable options exist. The CAESAR training set was collected using laser scanners, while other systems employ stereo photogrammetry. For example, the Temporal 3dMDBody™ scanner may be employed. Such a scanner provides full-body surface scans captured in about 1.5 ms.

In some embodiments, additional, or alternative categories may be utilized for labeling the training set.

In some embodiments, the scanned bodies can be utilized for generating training sets for a neural network algorithm to be able to identify a specific pathology for a scanned body provided as an input at the inference stage.

Optimizing the Body Model

In some embodiments, at step 202 in FIG. 2, the parametrized body model generated in step 200 is optimized to a target subject. In some embodiments, one or more target 3D scans of a target subject are received. The model generated at step 200 is then optimized and personalized to the target subject based on the target 3D scans, via a training process which minimizes a loss function which registers the body surface model to the target 3D scans. At the conclusion of step 202, a personalized target body surface model of the target subject is generated.

In some embodiments, target subjects may be scanned in a variety of poses, resulting in a series of surface scans (for example point clouds, triangulated meshes, splined surfaces, etc).

In some exemplary embodiments, an MRI or CT scanners can be used as a scanning mechanism. In some embodiments, such MRI or CT scanners can provide cloud of data points representing volumetric data or "voxel" sets. In some embodiments, the point cloud can be represented in a unified coordinate system. For example, such a coordinate system can have an x-axis, a y-axis and a z-axis coordinate system. In some other possible embodiments such a coordinate system may be an axel-axis system.

In some embodiments a registration process can align the surface scans within a unified coordinate system. For example, point clouds from depth cameras or from a CT scanning can be brought into a unified coordinate system. Such a unified coordinate system can be utilized for comparing and measuring body poses of scanned bodies with a body surface models. In some embodiments, the scanned bodies may be labeled according to the poses of the human subjects.

In some embodiments, classifying the target subject amounts to an optimization problem similar to the process described by Loper et al. The difference is that here, body parameters β specifically capture differences due to pathology, and influence the pose dependent deformations Q(β,θ). The optimization problem can be written as $$[\beta, \theta] = \operatorname{argmin}_{\beta,\theta} \int_{x_s \in T_s} \rho(x_s \in T_s \operatorname{MIN} \|x_s - x_t\|) + \lambda \sum_{r \in \theta_s} r^2 + \mu \sum_{b \in \beta} b^2 \quad (7)$$

where S is a scan, $T_s$ is the model mesh for a given scan, $\theta_s$ is the pose for a given scan, ρ is a robust distance metric such as Geman-McClure, and λ, μ are regularization weights. The last term assumes that body parameters are zero centered, and many other regularizations and penalty terms are possible (surface normal, contact with floor surface, color, etc).

In some embodiments, given proper initialization, this optimization can be performed with gradient descent algorithms. Body parameters β are those which best describe the subject, including pathologic deformations across all scans. For example, a scoliotic patient could be scanned both standing upright but also in the Adams forward bend posture; solving Eq. (7) would provide the parameters that best fit both scans, thereby providing a holistic model of the patient.

Figure 5:
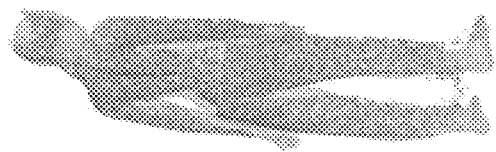
FIG. 5 shows an initialization and optimization of pose $\theta$ and body type $\beta$, according to exemplary embodiments of the present invention.
Figure 5:
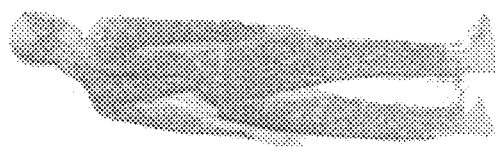
Figure 5:
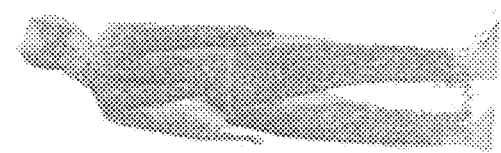
Figure 5:
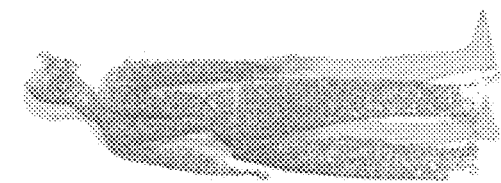

FIG. 5 shows the steps (from left to right) in a ample registration with initialization and optimization of pose and body type.

Having a parametric model of deformity will enable objective classification of body type in a way not currently possible. This would allow physicians to compare patient populations between hospitals. Perhaps even more significantly, an objective measure of body shape may prove instrumental in evaluating treatment options, such as varying surgical options or different bracing techniques as mentioned above.

Optical Scans

Equation (7) is agnostic to the source of surface data. In some embodiments, a low-cost and potentially portable system comprised of one or more depth cameras controlled by a computer that can record, and process optical scans can be used. In preliminary testing we have employed three Intel Realsense D435 cameras on a single host with a multi-threaded application.

Cameras are first calibrated to transform point clouds into a unified coordinate system. This can be accomplished by recording a calibration target (e.g. sphere) in many mutually visible locations. Rigid transformation between coordinate systems can be computed with SVD. Novel subjects can then be scanned in multiple poses and their body parameters found as described above.

Skeletal Estimation from Surface

At step 204, a computerized skeletal estimation model is trained to estimate skeletal (e., spinal) shape. In some embodiments, the training is based on a training set comprising (i) body surface models of a plurality of subjects, and (ii) skeletal landmarks sets of said plurality of subjects.

In some embodiments, the process of identifying the spine shape of a human subject from a three-dimensional image may be by utilizing at least one spine models representing spine deformations. In some embodiments such spine models can represent specific deformations, shapes, and/or skeletal structures. In some embodiments, these spine models can be utilized to train the skeletal estimation model to predict the spine shape of a human subject in the three-dimensional image surface model of a human subject given as an input at the inference stage.

In some embodiments, more than one spine model may be used, wherein each spine model may represent spine deformations and/or skeletal structure of a specific spinal deformity.

In some embodiments, the spine models may be defined with positions of vertebral landmarks designed to depict the shape of the spinal cord. In some embodiments, the vertebral landmarks can form a specific spine shape which can be associated with specific spinal deformity. In some embodiments, the vertebral landmarks positions can be identified by a unified coordinate system. For example, the landmark positions can be expressed with coordinate values.

Previous sections have demonstrated how parametric models can describe human surfaces and spine shape. The present disclosure now proposes, in some embodiments, a statistical model that can determine the relationship between these two surface body shape and skeletal (e.g., spinal) shapes.

In some embodiments, a triangle deformation model similar to SCAPE may be formulated, except in this case, the triangulated mesh is not a watertight shell. Each edge on the back of the template mesh is connected to each vertebral landmark of the template spine, giving a sort of clustered pyramid for each vertebra. The deformation model from template edges V* to model edges V is simply:

$$V_f = L_f V_f^*  \quad (8)$$

$$L = L_0 + \sum_{i=1}^{|\beta|} \beta_i L_i \quad (9)$$

where $L_f$ is a 3×3 deformation matrix for face f. The $\beta$ coefficients are the coefficients after mapping D into low dimensional space as described above.

Figure 6:
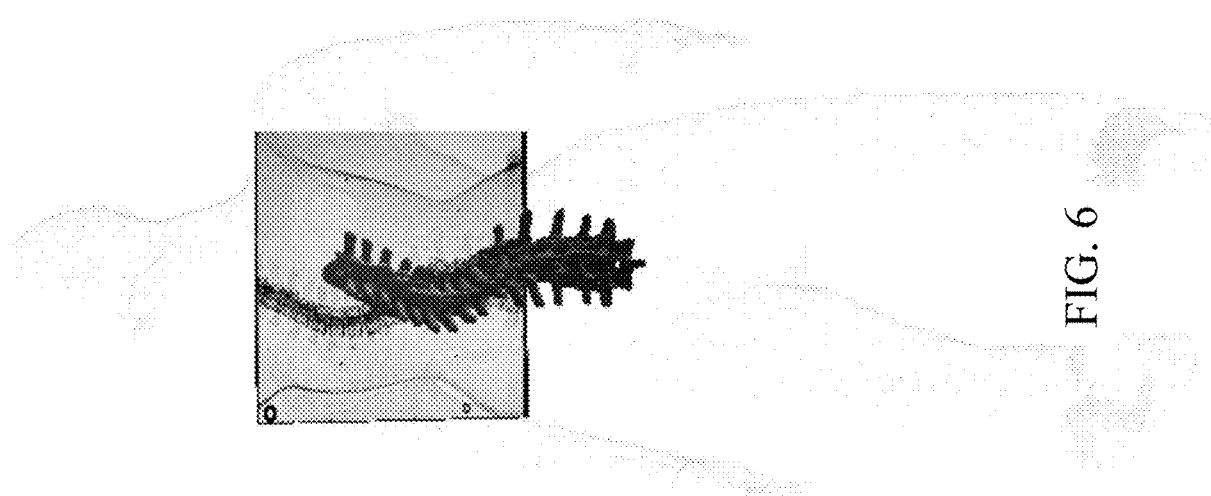
FIG. 6 shows a spine model and surface model in a shared coordinate space, according to exemplary embodiments of the present invention.

With reference to FIG. 6, in some embodiments, utilizing a unified coordinate system and techniques which are based on surface mesh can allow expressing areas on the body surface and the spine models on one coordinate system. In some embodiments, utilizing one unified coordinate system can allow determining the geometric relationship between the spine model and the surface of a human subject.

Given a training set of aligned surface meshes and skeletal landmarks (FIG. 5), L is found by minimizing the squared error between the model edges $V_f$ and the measured edges.

Once this model has been trained, it is possible to predict skeletal shape of novel subjects. For example, a patient could be scanned with depth cameras and body surface modeled as described above. Then skeletal landmarks can be estimated using Eq. (8).

Intermodal Data Collection

In some embodiments, an EOS™ slot scanner may be used to collect radiographic measures of spine shape. In some embodiments, several depth cameras may be positioned around the scan area such that they can record the human subject simultaneously with the radiography scanning, i.e., in a temporally-aligned fashion. In some embodiments, surface models may be fitted to the optical scan as described above. Parametric spine models can be constructed by fitting statistical models to the radiographic image. Four-spine modeling can be sufficient to use the semi-automated sterEOS reconstructions provided by EOS Imaging. Once a training set is collected with both these parametric models in a shared coordinate space it is possible to learn the statistical relation between them, as described above.

Assessment and Visualization

At step 206, the trained skeletal estimation model is applied to the calculated target body surface model of the target subject, to estimate a skeletal shape of said target subject.

In many skeletal pathologies, functional disability may be less of a concern than patient self-image. Surgeons may measure the success of an operation based on radiographic measures (e.g. coronal curve correction) while patients see the external expression. Unfortunately, there are few objective measures of surface deformity, and even fewer 3D parameters.

In this proposal body type coefficients $\beta$ can be read directly as a measure of deformity, as these values correspond to LDA classifications of the pathologic residual (after subtracting most PCA variance from normals). For example, the proposed LDA formulation for scoliotic patients is derived from the well documented and widely accepted Lenke classification system. It is therefore possible that physicians will feel comfortable interpreting and adopting these parameters.

More directly, the present disclosure proposes that these models can be employed in patient assessment. Body parameters will be used to track changes in patient surface shape after treatment, for example bracing or surgery. Furthermore, these parameters will be used as an objective measure of three-dimensional deformity by correlating with subjective appraisal by patients and clinicians. For example, it may be possible to find which model parameters correlate with improved patient reported surgical outcomes as measured by e.g. TAPS, or to develop a replacement questionnaire using 3D models in place of 2D sketches.

In some embodiments, the pathology type associated with the spine shape can be utilized to assess the skeletal shape.

Figure 7:
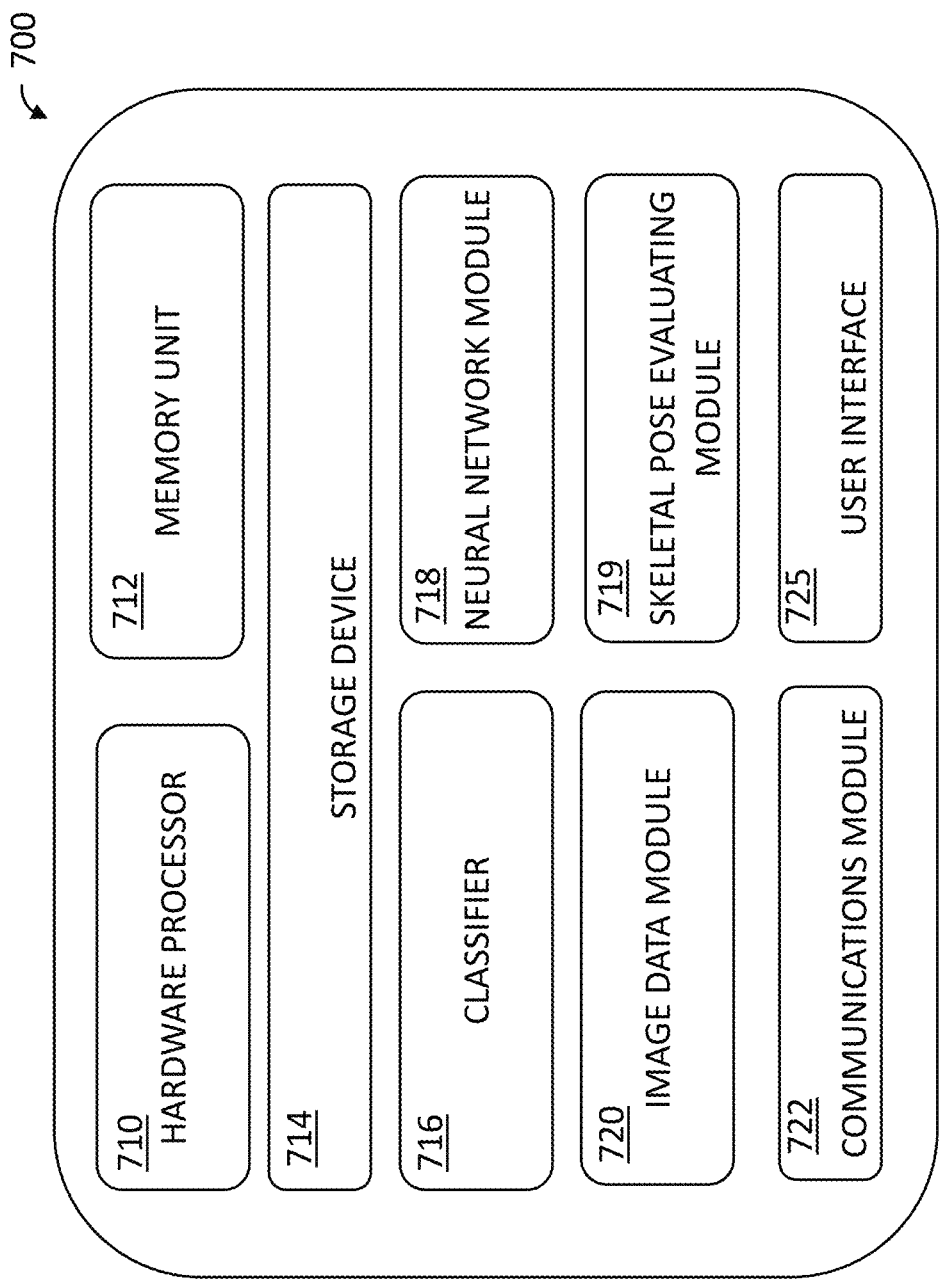
FIG. 7 shows a block diagram of an exemplary system according to an embodiment of the present invention.

FIG. 7 shows a block diagram of an exemplary system according to an embodiment of the present invention. FIG. 7 is a block diagram which in some embodiments, can be designed as a computer program product implementing at least some of the process and/or methods disclosed by the present disclosure.

System 700 as described herein is only an exemplary embodiment of the present invention, and in practice may have more or fewer components than shown, may combine two or more of the components, or a may have a different configuration or arrangement of the components. The various components of system 700 may be implemented in hardware, software or a combination of both hardware and software. In various embodiments, system 700 may comprise a dedicated hardware device, or may form an addition to/or extension of an existing device.

System 700 may store in storage device 714 software instructions or components configured to operate a hardware processor 710 comprising such as hardware processor (also "hardware processor," "CPU," or simply "processor"). In some embodiments, the software components may include an operating system, including various software components and/or drivers for controlling and managing general system tasks (e.g., memory management, storage device control, power management, etc.) and facilitating communication between various hardware and software components.

In some embodiments, the software components of the system 700 may comprise an operating system, including various software components and/or drivers for controlling and managing general system tasks (e.g., memory management, storage system control, power management, etc.) and facilitating communication between various hardware and software components.

In some embodiments, system 700 may comprise a hardware processor 710, a communications module 722, memory unit 712, storage device 714, a user interface 725, skeletal pose evaluating module 719, classifier 716, neural network module 718, and image data module 720.

In some embodiments, the image data module 720 can be configured to process the received image data. In some embodiments, such image data can depict a human subject. In some embodiments, the image data can depict a scanned human subject in a three-dimensional fashion. In some embodiments, the image data module 720 may be configured to store the image data in a memory unit 712.

In some embodiments, the image data module 720 may operate the communications module 722 for the purpose of receiving images from an external third-party device. In some cases, such the third-party device can be a computerized device designed to send, provide, and receive image data. In some embodiments, the communications module 722 may also be utilized by the system 700 for one or more communication tasks. Such communication tasks may be sending information and/or data to other computerized devices, communicate over a network, receive information or data, and the like.

In some embodiments, the image data module 720 may be configured to communicate with the user interface 725 for the purpose of displaying the images depicting human subjects to a user operating the system 700. Such images can be three-dimensional scans of bodies, body surface models, and the like.

In some embodiments, the user interface 725 may be configured to communicate with a display device (not shown) and display the images. In some embodiments, the user interface 725 can provide with one or more graphic interfaces designed to receive instructions and/or commands from a user. In some embodiments, such instructions can be provided by an input device such as mouse device, keyboard device, and the like.

In some embodiments, the image data module 720 may also be configured to receive computer instructions to administrate the images and/or the three-dimensional scans. In some embodiments such instructions can be received the memory unit 712. In some embodiments, the instructions can be received from an input device, e.g., keyboard or a mouse input device, controlled by a user.

In some embodiments, the image data module 720 may be configured to communicate with external computerized devices for the purpose of receiving the image data from a third-party entity such a remote computer or a remote database. In some embodiments, the image data module 720 may configured to communicate with digital storage mediums for the purpose of receiving image data. Such a storage medium can be SD storage, an external storage medium designed to store digital files, and the like.

In some embodiments, classifier 716, is a machine learning classifier which may be configured to be trained on a training set comprising a plurality of images depicting human subjects and labels, and classify each human subject in an image into specified classes according to one or more classification techniques and/or algorithms. In some embodiments, such classes may be spine deformities, poses if human subjects, and the like.

In some embodiments, the neural network module 718 is a module operated by system 700 and designed to communicate with a neural network layer which include the learning layers according to one or more neural network techniques and/or algorithms. In some embodiments, the neural network module 718 may be configured to communicate with a neural network algorithm for the purpose of learning from a training set.

In some embodiments, the neural network module 718 can be configured to utilize calculation procedures, and or formulas for the purpose of the training. In some embodiments such formulas, can be optimization formulas, objective functions, loss functions, and the like.

In some embodiments, the neural network module 718 can be configured to communicate with the skeletal pose evaluating module 719 for the purpose of estimating the spine deformities from a scan of a human subject. In some embodiments, the neural network module 718 can applied to a three-dimensional scan of a human subject residing in the skeletal pose evaluating module 719 for predicting the spine shape. In some embodiments, such a three-dimensional scan may be an optically scanned human subject.

In some embodiments, system 700 may operate the skeletal pose evaluating module 719 to receive image data from the image data module 720 and communicate with an external service neural network module 718.

In some embodiments, the neural network module 718 may utilize one or more neural network techniques and/or algorithms to determine the spine shape. In some embodiments, the spine shape may be determined, based on previously conducted training sessions configured to train the neural network module 718 to detect the spine shape of a body in a three-dimensional scan.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Rather, the computer readable storage medium is a non-transient (i.e., not-volatile) medium.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A method comprising:
    generating a parametrized three-dimensional (3D) body surface model, based, at least in part, on a training set comprising a plurality of 3D scans of subjects;
    receiving one or more target 3D scans of a target subject;
    optimizing said body surface model with respect to said one or more target 3D scans, based, at least in part, on minimizing a loss function which registers said body surface model to said target 3D scans, to calculate a target body surface model of said target subject;
    training a skeletal estimation model, based, at least in part, on a training set comprising:
    (i) body surface models of a plurality of subjects, and
    (ii) skeletal landmarks sets of said plurality of subjects; and
    applying said trained skeletal estimation model to said calculated target body surface model of said target subject, to estimate a skeletal shape of said target subject.

2. The method of claim 1, wherein at least some of said target 3D scans are labelled with a pose of said subject associated with a respective target 3D scan.

3. The method of claim 1, wherein said training of said 3D body surface model is configured to encode a body type parameter, based, at least in part, on a labeling of said training set with a skeletal deformity.

4. The method of claim 3, wherein said labelling is a scoliosis classification category selected from the group consisting of: main thoracic, double thoracic, double/triple major, and thoracolumbar/lumbar.

5. The method of claim 3, wherein said encoding is a low-dimensional encoding.

6. The method of claim 1, wherein said target 3D scans comprise at least one of: point clouds, triangulated meshes, and splined surfaces.

7. A system comprising:
    at least one hardware processor; and
    a non-transitory computer-readable storage medium having stored thereon program code, the program code executable by the at least one hardware processor to:
    generate a parametrized three-dimensional (3D) body surface model, based, at least in part, on a training set comprising a plurality of 3D scans of subjects,
    receive one or more target 3D scans of a target subject,
    optimize said body surface model with respect to said one or more target 3D scans, based, at least in part, on minimizing a loss function which registers said body surface model to said target 3D scans, to calculate a target body surface model of said target subject,
    train a skeletal estimation model, based, at least in part, on a training set comprising:
    (i) body surface models of a plurality of subjects, and
    (ii) skeletal landmarks sets of said plurality of subjects, and
    apply said trained skeletal estimation model to said calculated target body surface model of said target subject, to estimate a skeletal shape of said target subject.

8. The system of claim 7, wherein at least some of said target 3D scans are labelled with a pose of said subject associated with a respective target 3D scan.

9. The system of claim 7, wherein said training of said 3D body surface model is configured to encode a body type parameter, based, at least in part, on a labeling of said training set with a skeletal deformity.

10. The system of claim 9, wherein said labelling is a scoliosis classification category selected from the group consisting of: main thoracic, double thoracic, double/triple major, and thoracolumbar/lumbar.

11. The system of claim 9, wherein said encoding is a low-dimensional encoding.

12. The system of claim 7, wherein said target 3D scans comprise at least one of: point clouds, triangulated meshes, and splined surfaces.

13. A computer program product comprising a non-transitory computer-readable storage medium having program code embodied therewith, the program code executable by at least one hardware processor to:
   generate a parametrized three-dimensional (3D) body surface model, based, at least in part, on a training set comprising a plurality of 3D scans of subjects;
   receive one or more target 3D scans of a target subject;
   optimize said body surface model with respect to said one or more target 3D scans, based, at least in part, on minimizing a loss function which registers said body surface model to said target 3D scans, to calculate a target body surface model of said target subject;
   train a skeletal estimation model, based, at least in part, on a training set comprising:
   (i) body surface models of a plurality of subjects, and
   (ii) skeletal landmarks sets of said plurality of subjects; and
   apply said trained skeletal estimation model to said calculated target body surface model of said target subject, to estimate a skeletal shape of said target subject.

14. The computer program product of claim 13, wherein at least some of said target 3D scans are labelled with a pose of said subject associated with a respective target 3D scan.

15. The computer program product of claim 13, wherein said training of said 3D body surface model is configured to encode a body type parameter, based, at least in part, on a labeling of said training set a said skeletal deformity.

16. The computer program product of claim 15, wherein said labelling is a scoliosis classification category selected from the group consisting of: main thoracic, double thoracic, double/triple major, and thoracolumbar/lumbar.

17. The computer program product of claim 15, wherein said encoding is a low-dimensional encoding.

18. The computer program product of claim 13, wherein said target 3D scans comprise at least one of: point clouds, triangulated meshes, and splined surfaces.

* * * * *